(12) United States Patent
Agrawal et al.

(10) Patent No.: US 6,482,632 B1
(45) Date of Patent: Nov. 19, 2002

(54) BACTERIOPHAGE, A PROCESS FOR THE ISOLATION THEREOF, AND A UNIVERSAL GROWTH MEDIUM USEFUL IN THE PROCESS THEREOF

(75) Inventors: Pushpa Agrawal; Vishal Soni, both of Chandigarh (IN)

(73) Assignee: Council of Scientic and Industrial Research, New Delhi (IN)

( * ) Notice: Subject to any disclaimer, the term of this patent is extended or adjusted under 35 U.S.C. 154(b) by 0 days.

(21) Appl. No.: 09/295,851

(22) Filed: Apr. 21, 1999

Related U.S. Application Data

(63) Continuation-in-part of application No. 09/277,916, filed on Mar. 29, 1999, now abandoned.

(51) Int. Cl.[7] ............................. C12N 7/00; C12N 7/02; C12N 1/21; C12N 15/00
(52) U.S. Cl. ................. 435/235.1; 435/239; 435/252.3; 435/252.31; 435/252.33; 435/252.35; 435/252.8; 435/252.5; 435/253.1; 435/253.5; 435/472; 435/473; 435/476; 435/485; 435/486; 435/488
(58) Field of Search ........................... 435/235.1, 252.3, 435/252.1, 252.31, 239, 252.33, 252.35, 252.8, 252.5, 253.1, 253.5, 472, 473, 476, 485, 486, 488

(56) References Cited

FOREIGN PATENT DOCUMENTS

| EP | 0184086 | 6/1986 |
|---|---|---|
| EP | 0281356 | 9/1988 |
| EP | 0403173 | 12/1990 |

OTHER PUBLICATIONS

Loftus et al. Current Microbiology 30 (5):p317–321 1995.*

Balan et al. Brazilian Journal of Genetics 20 (4):p547–552, Dec. 1997.*

Schneider et al. System. Appl. Microbiol. 14:p72–78, 1991.*

Schneider, J. et al. "preliminary Characterization of Actinophages of the Thermophilic . . . " Intervirology (vol. 30), No. 6, (1989) pp 323–329.

* cited by examiner

Primary Examiner—Mary E. Mosher
(74) Attorney, Agent, or Firm—Ladas & Parry

(57) ABSTRACT

The present invention provides a isolated bacteriophage useful as a tool for studying biological, biochemical, physiological and genetic properties of actinomycetes and other organisms which comprises a novel strain of Saccharomonospora having certain specified characteristics. The invention also relates to a process for the isolation of the said bacteriophage and/or DNA phage and to a novel universal growth medium which is particularly useful in the said process. Another embodiment of the process relates to a cloning vector which comprises a plasmid or bacteriophage comprising the phage DNA of the invention.

33 Claims, 1 Drawing Sheet

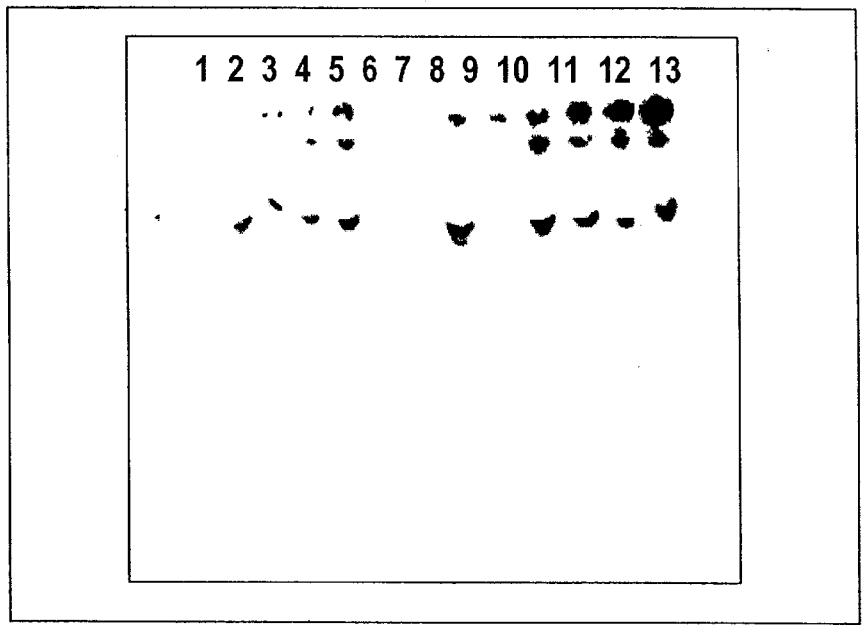

1. uninoculated medium
2. Amycolata mediterranei non lysogen
3. AR4   a lysogen of A.mediterranei    Batch 1
4. AR4   "                              Batch 2
5. AR10  "                              Batch 1
6. AR10  "                              Batch 2
7. AR17  "                              Batch 1
8. AR18
9. AR35  "                              Batch 1
10. AR17 "                              Batch 2
11. AR35 "                              Batch 2
12. AR35 "                              Batch 3
13. AR35 "                              Batch 4

AR = Code names for the A.mediterranei lysogens.
Experimental details are in example Number 12. Thin Layer chromatograph showing difference in the metabolites produced by different lysogens and non lysogen.

BACTERIOPHAGE, A PROCESS FOR THE ISOLATION THEREOF, AND A UNIVERSAL GROWTH MEDIUM USEFUL IN THE PROCESS THEREOF

The present application is a continuation-in-part of application Ser. No. 09/277,916 filed on Mar. 29, 1999, now abandoned.

This invention relates to an isolated bacteriophage and a process for preparation of said bacteriophage useful as a tool for studying biological, biochemical, physiological and genetic properties of actinomycetes and other organisms. The bacteriophage obtained by the present invention is particularly useful for the characterization of antibiotic biosynthetic pathways and similar primary and secondary metabolic pathways. The bacteriophage described in this process may also be used for the study of several other genetic and physiological pathways. It may also be used to generate mutations in the metabolic pathways of bacteria, and after some specific alteration such as after cloning into suitable mobilising vectors, may also be used to study the metabolic pathways of other microorganisms and plants. Mutations can be generated essentially at any locus of the bacteria. The results of the above mentioned alterations or mutations may lead to the production of new metabolic products or to the expression of new physiologically active compounds or to the expression of novel characteristics either in the same host or in heterologous hosts.

BACKGROUND OF THE INVENTION

As used in this application, bacteriophage or phage refers to a virus or viruses which infect bacteria. After infection the virus can produce new progeny particles or can remain dormant within the bacterial genome. Lysogen is a bacteria which carries a bacteriophage without being harmed. Plaque is a turbid/clear spot produced due to lysis of the cells infected by a bacteriophage. Prophage is a bacteriophage that is maintained in the lysogenic state in a bacterial cell. Confluent lawn is a uniform growth of organism on an agar plate. Phagemid is a plasmid vector carrying some part of the phage DNA. The term restriction enzyme refers to an endonuclease that cuts DNA sites defined by its recognition sequence. Auxotroph is a bacterial strain defective for the synthesis of one or more sugar or amino acids. Restriction barrier is intended to mean a host defense system which protects the bacteria from invaders, by cleaving the invaders' DNA. Cloning is understood to mean the procedure for the generation of recombinant DNA. Genetic tool is a system where DNA is used as a tool. Mutation is an alteration in the sequence of bases in the DNA of an organism. This alteration may be caused by insertion, deletion or modification of DNA bases. Transposon refers to a genetic element that carries the information that allows it to integrate at various sites in the host genome. Genome is a term used to describe the complete genetic complement of a virus, or cell or bacteria or any living organism.

The process of the present invention involves the isolation from soil samples and purification of a novel bacteriophage from a strain of Saccharomonospora called PA136. The strain of Saccharomonospora described in the present invention is characterized by the presence of single lateral white coloured spore, meso-diaminopimelic acid; arabinose and galactose as total sugar but no mycolic acid and major components of fatty acids—16 carbons iso- and antiso fatty acids. Other properties of this strain are: it grows on hypoxanthine, hypoxanthine+0.3% glucose, tributyrine, xylitol, thallous acetate, thallous acetate+0.1% glucose, propanol, butanol-1, 3 diol, D-fucose, salicin, arabinose, L-asparagine, phenylalanine, L-serine, and sodium benzoate. The strain grows in the temperature range of 20° C. to 55° C. on an agar plate with pH range 5.5 to 9.0. It is catalase positive and produces extracellular enzymes lipase (C14), leucine arylamidase, valine arylamidase, cystein arylamidase, trypsin, chemotrypsin, acid phosphatase, naphthol As-B1-phosphophydrolase, α-glucosidase and β-glucosidase. The chemical composition of the total cell is as follows: meso-di-aminopimelic acid, arabinose, galactose, phosphatidyl glycerol, di-phosphatidyl glycerol, phosphatidyl ethanolamine, hydroxyphastidyl ethanolamine, phosphatidyl inositol glycolipids are present. Sugar containing unidentified groups of phospholipids is present. Total fatty acids are: major components of 16 carbon iso- and antiso-fatty acids of branched and straight chain carbon compounds. It does not utilise sucrose. It mostly produces a diffusable pigment that is either green, orange or yellow. Sometimes the strain Saccharomonospora PA136 does not produce any pigment at all. At times the pigment is non-diffusable. However, the pigments produced by the strain Saccharomonospora PA136 are water-soluble. The pigments are insoluble in either, ethanol, methanol, butanol, isopropanol, benzene, ethyl acetate, chloroform and acetone. It is partially soluble in phenol. The green pigment produced by the strain is a characteristic of the genus Saccharomonospora. The strain Saccharomonospora PA136 undergoes autolysis after 5–6 days of incubation on a culture plate which when subjected to detailed analysis results in the isolation of a bacteriophage named as PIS136. This temperature bacteriophage has a wide host range amongst Gram positive (Gram+) bacteria and generates lysogens at the rate of 2 to 3 percent of the total cells infected. The phage PIS136 has a DNA genome of about 90 kb where the GC (Guanidine and Cytosine) content is 69 to 71 mole percent. The genome of this phage is partially methylated and lacks recognition sites for many restriction enzymes. The phage genome or bacteriophage that has the property of generating random mutations by transposition also shows the phenomenon of gene inversion. The phenomenon of gene inversion can be used to control the host range of the phage as well as for heterologous and conditional expression of genes. The phage has been deposited as a lysogen of the strain Saccharomonospora PA136 at the Microbial Type Culture Collection, Institute of Microbial Technology, Chandigarh and carries an accession number MTCC A0001, where 'A' stands for Actinomycetes and also bears the depository number DSM 12317 at DSMZ-DEUTSCHE SAMMELUNG VON MIKROORGANISMEN UND ZELLKULTUREN GmbH where it was deposited on Jul. 16, 1998. Because of the unique properties this phage has immense potential as a genetic tool and can be used variously as a transposon for the generation of mutants, as an intergeneric cloning vector, for the study of metabolic pathways, as a reporter phage, for conditional gene expression, or even for the activation of silent genes, etc.

Bacteriophages or phages, the viruses of bacteria, are the simplest of all living organisms. They have been natural objects of study in attempts to understand life at the molecular level. Phages have evolved a number of regulatory schemes to ensure efficient production of progeny particles during development. However, in general, in about 1% of the cells that are infected by the temperature phages, lysogeny is established, that is when the phage genome integrates with the host. The lysogens are immune to super-infection.

Numerous phages have been isolated from industrially and medically important bacteria such as Streptomyces species, Corynebacterium species, *Lactococcus lactis*, Mycobacteria, *Escherichia coli*, Salmonella and Staphylococcus species etc.

About 70% of the known and naturally occurring antibiotics are produced by members of the genus Streptomyces. In most cloning procedures for Streptomyces species, plasmid based vectors capable of replicating autonomously have been used (Rao, R. N., Richardson, M. A. and Kuhtoss, S. 1987 in *Methods in Enzymology*, 153: 166–198; Hopwood, D. A., Bibb, M. J., Chater, K. F. and Kieser, T. 1987 in *Methods in Enzymology*, 153: 116–165).

At the same time the relatively broad host range temperature bacteriophage ØC31 (which infects Streptomyces species and the related genus Streptoverticillium species only) was developed as a versatile containing vector (Chater, K. F. 1986, In *The Bacteria*, Vol. IX. Queener, S. W. and Day, L. E. (ed) London: Academic Press pp 119–158, Kobler, L., Schwertfirm, G., Schmieger, H., Bolotin, A. and Sladkova, I. 1991 *FEMS Microbiology Letters*, 8: 347–354; Bruton, C. J., Guthrie, E. P. and Charter, K. F. 1991. Bio/Technology, 9, 652–656). In 1991, Kuhtoss, S., Richardson, M. and Rao, R. N. (*Gene*, 97: 143–146) developed a shuttle vector which utilizes the site specific recombination system of the phage ØC31. The vectors allow the cloned DNA to be stably inserted into a host cell. McHenny, M. A. and Baltz, R. H. (*Journal of Bacteriology*, 1988 170: 2276–2282) claimed to have developed a transduction system for several species of Streptomyces and related genera using the phage FP43 but this system failed on a very important strain of *Streptomyces hygroscopicus* 10–22. Thus Zhou, X., Deng, Z., Hopwood, D. A. and T. Kieser, (1994 *Journal of Bacteriology*, 176: 2096–2099) used a new phage ØHAU3 which has a relatively broad host range within Streptomyces and developed a phagemid to study the molecular biology of the *Streptomyces hygroscopicus* strain 10–22.

Phages of another industrially important organism, *Lactococcus lactis* have also been exploited for vector development. (Kok, J., Van der Vossen, J. M. B. M. and G. Venema. 1984 *Applied Environmental Microbiology*, 48: 726–731; Vander Vossen, J. M. B. M., Van der Lelie, D. and Venema, G. 1987 *Applied Environmental Microbiology*, 53: 2452–2457). Attempts have also been made to develop the L5 phage of mycobacteria into a suitable vector in order to simplify the study of the molecular biology of mycrobacteria (Lee, M. H., Pascopella, L., Jacobs, W. R. and G. F. Hatfull. 1991 *Proc. Natl. Acad. Sci. USA*, 88: 3111–3115; Donnelly-Wu, M. K., Jacobs, Jr. W. R. and G. F. Hatfull. 1993 *Molecular Microbiology*, 7: 407–417). In spite of all these studies, the application of molecular techniques has not yet led to dramatic results in industrial strain development programmes or in the development of hybrid or new antibiotics. However, none of the phages of Gram positive (Gram+) bacteria that have been reported in the literature have the property of being a transposon.

A transposon has the property that it can insert itself at random sites within the host genome. By virtue of their insertion properties, transposons have been used to improve the production of secondary metabolites and to construct strains that will produce hybrid or new secondary metabolites. Transposons have also been used for gene disruption and to clone global regulatory genes, pathways of secondary metabolites and strong or regulatory promoters. They might also be used to block competing or unnecessary pathways in order to achieve more efficient production of secondary metabolites (Hahn, D. R., Solenberg, P. J., McHenny, M. A. and R. H. Baltz, 1991, *Journal of Industrial Microbiology*, 7: 229–234).

The present invention is thus based upon the need to develop a system with which one may be able to study the molecular biology of the class of Gram+ bacteria which contains a large number of organisms, such as species of Amycolatopsis, Corynebacterium, Mycobacteria, Nocardia, Micromonospora, Rhodococcus, Streptomyces etc., which are of both industrial and medical importance. At present there is no known multipurpose transposon or phage mediated vector or generalised transduction system available with which the genetics and molecular biology of these organisms can be studied without any problem. Further, most of these organisms are industrially very important because they produce antibiotics, enzymes, small peptides which are bio-active, glutamic acid and many other amino acids as secondary metabolic products. The regulation of these pathways is extremely complicated as several intermediates and precursor compounds are required for biosynthesis. In general, the secondary metabolic pathways within an organism are interrelated in that either they use same precursor molecule or one uses an intermediate compound of other as precursor. This may result in the poor production of the desired end product of one of the pathways compared to its related pathway. As the production level is very low with natural isolates, the goal of obtaining a high producer strain presents a major challenge to industry. Furthermore, most of the natural isolates also produce more than one secondary metabolite and the presence of another compound is often undesirable. Thus a bacteriophage having a property which can be used to stop the production of undesirable compounds by mutation will stop the diversion of a precursor compound from one pathway to another, which is often a limiting factor, will be very useful to industry. The property of gene inversion in the bacteriophage/phage described in the present invention may be used to overcome the problems that arise when an intermediate product of one pathway is a precursor molecule in other pathway. The process herein will be that the that the inverting fragment will be cloned in one of the biosynthetic pathways in such a way that when the inverting fragment is in one orientation the pathway will function normally, however, when it is in the other orientation the biosynthesis will be stopped at the point at which the inverting fragment is inserted. However, other part of the pathway that is functioning normally will allow the accumulation of intermediate products that may be used by some other biosynthetic pathway. Since the process of inversion can be externally controlled, it may be possible to modulate the biosynthetic pathways as per need. Thus the bacteriophage described in the present invention will bring a revolution, particularly to those industries that are involved in the commercialization of useful secondary metabolites produced by the microorganisms. This phage also infects mycobacteria and mutants of mycrobacteria can be obtained. These mutants may be used as live vaccines. Thus this invention establishes the possibility to have a transposon-phage which can be exploited as a generalized transduction system for several genera of Gram+ bacteria.

In the preparation of the bacteriophage, the choice of the growth medium is very important. Several known media such as (1) Luria Bertani (LB) having the composition per 1000 ml; 10 gm Tryptone, 5 gm Yeast extract, 10 gm Sodium Chloride; (2) Yeast extract: malt extract per 1000 ml; 2 gm Yeast extract, 4 gm Malt extract, 10 gm Glucose; (3) Tryptic Soya broth per 1000 ml; 17 gm Pancreatic Digest of casein, 3 gm Papaci digest of Soya meal, 5 gm Sodium Chloride, 2.5 gm Dibasic Potassium Phosphate, 2.5 gm Dextrose and (4) Bennett's medium containing per 1000 ml: 1 gm yeast extract, 1 gm Beef Extract, 2 gm Pancreatic digest of casein, 10 gm Dextrose, were tested and found that none of the media favoured the release of large amount of phage particles.

The components of the known media listed above are not easily assimilable and do not appreciably favour the lytic cycle of the phage. Further, all the above media lack trace elements that are very important for the growth of live organisms which ultimately may affect the lytic cycle of the bacteriophage. Accordingly, one embodiment of this invention relates to a growth medium, useful, inter alia, for fungi and bacteria, particularly, strain of Saccharomonospora called PA 136 which is a lysogen of the phage PIS 136.

The main object of the invention therefore, is to prepare a bacteriophage that may be useful as a genetic tool for studying the biological, biochemical, physiological and genetic properties of a large number of actinomycetes genera and other Gram+ bacteria. The process involves steps such as isolation and purification of a novel temperature bacteriophage (or phage), from a species of Saccharomonospora called PA136 and where either the phage or its bacteriophage can be used as a genetic tool to study the molecular biology and other properties of a large number of Gram+ bacteria. The species Saccharomonospora PA136 is a lysogen and upon lysis yields the wide host range mutagenic bacteriophage PIS136.

Another object of the present invention is to use the bacteriophage described herein, or the phage as a transposon and then in the generation of random mutations in a wide range of bacteria or any other suitable host.

Yet another object of the present invention is to use the invertible fragment of the phage cloned into a suitable vector to control/regulate the secondary metabolic pathways either of the host strain or of a heterologous host. The phage PIS136 can overcome the restriction barriers of many of the actinomycetes strains and establish itself as a lysogen by integrating into the host genomes at random sites.

It is yet another objective of this invention to prepare a universal growth medium which supports the growth of a large number of organisms belonging to various groups such as fungi, Gram− and Gram+ bacteria, particularly, strain of Saccharomonospora PA 136.

It is yet another objective of this invention to develop a medium which can shorten the time required for growth, which can produce large amount of exponentially growing cells and also which can withstand relatively high temperature of growth without having an adverse effect on the growth pattern.

It is another object of the invention to provide a growth medium that possesses essential trace elements necessary for growth of live organisms.

It is yet another object of the invention to provide a medium that induces the lytic growth of bacteriophage, particularly the phage PIS 136.

SUMMARY OF THE INVENTION

Accordingly, the present invention provides a isolated bacteriophage useful as a tool for studying biological, biochemical, physiological and genetic properties of actinomycetes and other organisms which comprises incubating a novel strain of Saccharomonospora having characteristics as herein described.

The present invention also provides a process for the isolation of a bacteriophage as a tool for studying biological, biochemical, physiological and genetic properties of actinomycetes and other organisms which comprises incubating a novel strain of Saccharomonospora having characteristics as herein described in a nutrient medium such as herein described until the autolysis stage is reached, isolating and purifying from the said medium a bacteriophage generated in the lysed culture by conventional methods, then breaking-up the proteinaceous envelop of the said isolated bacteriophage by known methods followed by recovering the bacteriophage by conventional precipitation techniques.

The present invention also provides a novel growth medium and a process for the preparation thereof useful for fungi and bacteria, particularly, strain of Saccharomonospora PA 136.

In an embodiment of the present process the subject matter a microorganism is a novel isolate of the genus Saccharomonospora and has taxonomic characteristics typical of the genus.

In another embodiment of the present process the novel isolate may be grown in any medium comprising varying quantities of beef extract, yeast extract, tryptone, tryptose, peptone, proteose peptone, malt extract, glucose, calcium chloride, magnesium chloride, ferric ammonium citrate, cobalt chloride at pH 7.0 to 7.5. However, the preferred medium comprises beef extract, tryptose, proteose peptone, yeast extract, glucose, calcium chloride, magnesium chloride, ferric ammonium citrate, cobalt chloride at pH 7.2, on quantities as particularly as described herein.

In yet another embodiment the isolate upon incubation for 3–6 days helps the release of the phage PIS136 in to the medium. However, the best result are obtained from fifth day onwards.

In another embodiment the isolated bacteriophage has about 90 kilobase pairs of lond double stranded DNA genome with guanidine and cytosine content of 69–71 percent.

In yet another embodiment the phage may be purified by using a modified procedure of Yamamoto et al., 1970 and Smorawinska et al., 1988 (Yamamoto, K. R.; Alberts, B. M., Benzinger, R., Lawhorne, L. and Treiber, G., 1970 Virology, 40: 734–744; Smorawinska, M., Denis, F., Dery, C. V., Magny, P. and Brzenski, R. 1988. Journal of General Microbiology, 134: 1773–1778).

In another embodiment, the invention also relates to a cloning vector which comprises a DNA molecule of the phage, and may comprise a plasmid or a bacteriophage.

In yet another embodiment the phage so obtained may be used to generate mutations in the metabolic pathways of bacteria and after some specific alteration such as after cloning in to suitable mobilising vectors, may also be used to study the metabolic pathways of other micro organisms and plants. The results of the above mentioned alterations or mutations may lead to the production of new metabolic products or to the expression of new physiolocial active compounds or may change the pathogenic property of an organism but maintain the immunogenic property which would enable the organism to be used as a live vaccine strain or to the expression of novel characteristics either in the same host or in heterologous hosts.

The novel growth medium of the invention is prepared by mixing the appropriate quantities of the following chemicals and complex media components such as: Beef extract or Lab Lamco, Yeast extract, Tryptose, Protease peptone, Soluble starch, Dextrose, and traces of Cobalt chloride or Cobalt nitrate and Ferric ammonium citrate. The composition when established and dissolved in double gas-distilled water, at room temperature, has a pH from about 6.0 to 6.6. This medium when used as it is, or after adjusting the pH between 7.0 and 7.2 by using 1N Sodium hydroxide acts as a universal medium for the growth of large number of actinomycetes genera, other Gram+ bacteria, some Gram- bacteria and for several groups of fungi. In particular, it was useful as an excellent medium for the growth of strain of Saccharomonospora PA 136.

Thus, the present invention provides for a process for the preparation of a universal growth medium useful for fungi and bacteria which comprises mixing of A, B and C, i.e. macronutrients, micronutrients and trace elements in the quantities mentioned as below:

A. macronutrients in the form of assimilable carbon sources such as:
  1. Lab Lamco or Beef extract 8–12 gm
  2. Starch 1–2 gm
  3. Dextrose 10 to 12 gm and
  also in the form of assimilable nitrogen sources such as:
  1. Protease peptine 1–3 gm
  2. Tryptose 1–3 gm B. micronutrients selected from yeast extract 1–3 gm, a and C. trace elements selected from:
  1. Cobalt chloride or nitrate 5–10 mg
  2. Ferric ammonium citrate 5–10mg
  3. Magnesium sulphate or chloride 0–10 mM
  4. Calcium chloride or nitrate 0–10 mM;

and thereafter making the volume to 1000 ml by the addition of double-distilled water.

BRIEF DESCRIPTION OF THE FIGURE

The FIGURE shows thin-layer chromatography of metabolites produced by PIS 136 lysogens and non-lysogens of *Amycolatopsis mediterranei*.

DETAILED DESCRIPTION OF THE INVENTION

The detailed process of the present invention involves the following steps:

Isolation of the strain Saccharomonospora

Soil samples were collected from a depth of 6 to 18 inches below the surface of an active compost heap in Northumberland, a county in UK and from Tokyo, Japan. The samples were first air dried at room temperature so as to kill those organisms that are sensitive to drying and then heated at about 100° C. and cooled to the room temperature.

One gram of each of the samples collected and pretreated as above were suspended in sterile water and vortexed. One ml of each of the suspensions were plated on a conventional medium containing sodium salt of Humic acid, Calcium carbonate, Ferrous sulphate and Potassium chloride, Magnesium sulphate, Disodium Hydrogen phosphate in distilled water at a pH more than 7.0 and was supplemented with cycloheximide, nystatin, nalidixic acid, penicillin G and polymyxin B.

The plates were incubated for a period ranging between 2 and 5 weeks. Each colony from the plate was subcultured on a medium containing measured quantities of Beef extract, Tryptose, Yeast extract, Proteose peptone, Dextrose, Calcium nitrate or Calcium chloride, Magnesium chloride or Magnesium sulfate, trace of ferric ammonium citrate, trace of Cobalt chloride or Cobalt nitrate and soluble starch in distilled water maintaining the pH of the medium between 6.0 and 8.5. The culture plates were incubated and the colonies producing green pigments were purified on a novel medium described later in this specification.

Identification of the Strain

All the colonies which produced green pigment were replanted on the above said novel medium using McCartney's bottles. A sample of each isolate was also preserved in glycerol using the said medium at a temperature below minus 20° C.

The colonies producing green pigment thus obtained were identified by the standard procedures such as morphology, substrate utilization such as carbon source, nitrogen source, and production of extracellular enzymes and chemical composition of the total cell (chemotaxonomy). The presence of a single lateral white coloured spore, meso-diaminopimelic acid; arabinose and galactose as total sugar but no mycolic acid and major amount of 16 carbon iso and antiso fatty acids, classified the strain as a member of the group actinomycetes, and identified the strain PA136 as a species of the genus Saccharomonospora.

It was observed that the cultures that produced green pigment start lysing after 5–6 days of incubation. However, subculturing of cells from the lysed area into fresh medium resulted in the growth of the same organism which lysed again. This experiment was repeated several times and each time the result was identical. The results suggested that the lysis is not 100% and the cause of the lysis is inheritable.

The phenomenon of autolysis or induced lysis described above was also observed in the liquid culture and the release of bacteriophage was found to be the cause of lysis.

Isolation and Purification of the Phage

It was observed that the strain Saccharomonospora PA136 undergoes lysis after 3–6 days incubation on a culture plate containing any of the following media:

1. Medium containing: Beef extract, Yeast extract, Tryptose, Proteose peptone, Dextrose, Calcium chloride, Magnesium chloride, Agar and distilled water to make it 1000 ml and maintained at a pH between 6.8 and 7.5.

2. Tryptic Soya Agar/Broth containing, pancreatic digest of Soya meal, Sodium chloride, Dibasic Potassium phosphate, Dextrose, Agar, double distilled water to make it 1000 ml, and pH maintained between 6.8 and 7.5.

3. Yeast extract-Malt extract medium containing yeast extract, Malt extract, Glucose, Agar, Double distilled water to make it 1000 ml, maintained at a pH between 6.8 and 7.5.

Lysis of the culture in a plate was observed upto the incubation temperature 55° C.

All the three media above may also be used both for autolysis and induction.

4. The novel medium described later below was inoculated with 5–6 loopful of actively growing culture of PA136 and incubated at about 25° C. for about 36 to 40 h and was then used to inoculate a large scale medium. Inoculum density was between 5% and 10% and the culture was grown between 25° C. to 30° C. This culture lysed after 4–5 days of incubation either at 25° C. to 30° C. or by shifting to 39° C. to 42° C. for 30 min to 6 hours.

In yet another experiment 2 day old culture was exposed to short wavelength UV from about 10 to 40 seconds and was then used to inoculate 300 ml of medium (1000 ml flasks). This culture lysed faster than the one which was not exposed to UV. If the UV exposure was more than 40 seconds (that is 60 seconds) it took 7 to 10 days to reach to the lytic stage because the initial growth was extremely slow.

From any of the cultures autolysed or induced, the original PA 136 strain could be recovered and the phage PIS136 could be purified.

The phage was purified by the standard method of Yamamoto et al., 1970 and Smorawinska et al., 1988 (Yamamoto, K. R., Alberts, B. M., Benzinger, R., Lawhorne, L. and Treiber, G., 1970 Rapid bacteriophage sedimentation in the presence of polyethylene-glycol and its application to large scale virus purification. Virology, 40: 734–744; Smorawinska, M., Denis, F., Dery, C. V., Magny, P. and Brzenski, R. 1988. Characterization of SE-3, a virulent bacteriophage of *Saccharopolyspora erythraea*. Journal of General Microbiology, 134: 1773–1778), with a minor modification in that pelleting was done at 35000 rpm for about four hours.

A process as claimed in claims 10–14 were precipitation of polynucleotide is carried out in the presence of 0.25M Sodium chloride and a solution of 0.15M sodium chloride and 0.015M tri-sodium citrate, at 4° C. in presence of ethanol.

Further characterization of the bacteriophage by electron microscopy was done by the standard procedure for example-negative staining using phosphotungstic acid at neutral pH.

The bacteriophage does not have sites for the restriction enzymes marked by *, but are sensitive to the other restriction enzymes listed herein:

*Ava I, *Ase I, BamHI, *Bgl II, *Dpn I, *Dra I, EcoRI, *Hind III, *EcoR V, Kpn I, *Pst I, *Xba I, *Xho I, BstE II, BstX I, Alu I, Sau3A I, Sph I (refractory), Sfi I, Cla I, Nco I, Mlu I, Sac I, Sac II, Sca I, Sal I, Sma I, Stu I, Pvu II, Xma I, Nhe I, Spe I, SnaB I, Not I, Xmn I, Msp I, Hpa II, Mbo I, Hae III, Hha I, *Nsi I, Nar I, Age I, BstN I (these are the standard names followed all over the world. These products are sold by different companies by their standard names as described here).

The phage/bacteriophage infects the following strains of actinomycetes: *Streptomyces albusG* (D. A. Hopwood), *Streptomyces albus* (Sal I defective mutant) (D. A. Hopwood), *S. albunaceus, S. achromogenes* subsp., *achromogenes* (DSM 40028), *S. coelicolor* A3 (2) (D. A. Hopwood), *S. coelicolor* ØC31 sensitive mutant, (D. A. Hopwood), *S. clavuligerus* (NRRL-B 3585), *S. canescnes* (ISP 5001), *S. galileus* (K. Dharmalingam), *S. hygroscopicus* (ISP 5578), *S. lividans* (D. A. Hopwood) *S. varsoviensis* (DSM 40346), *S. vastus* (DSM 40309), *S. vinaceus* (DSM 40257), *Saccharopolyspora erythreus,* (NRRL-B 5616), *Saccharothrix aerocolonigenes* (DSM 40034), *Streptoverticillium albireticuli* (DSM 40051), *Microtetraspora inositola* (DSM 43189), *Micromonospora pusilla* (IFO 14684), *Actinomandura madurae* (IFO 14623), *Amycolatopsis mediterranei* (ATCC 27643), *A. mediterranei* (ATCC 21789), *A. medterranei* (ATCC 21271), *A. mediterranei* (13685), *Nocardia amarae* (*Gordona amarae*), *Mycobacterium fortuitum, Mycobacterium smegnatis, Bacillus subtilis.*

Recovery of Phage DNA

The standard method of phage DNA preparation was modified to suit the phage PIS 136: proteinaseK and SDS (Sodium dodecyl-sulphate) treatment was supplemented with β-mercaptoethanol, Triton X-100 (octylphenoxy polyethyl ethanol) and a longer incubation was given in the temperature range 37° C.–53° C. The sensitivity of the said bacteriophage or phage DNA to the restriction enzymes and methylation was checked by the standard procedure.

The host range of the bacteriophage PIS136 was checked by standard procedures either by spotting serial dilution of the phage preparation on the lawn of the test strains or by infecting the single cell culture, spore or mycelium or the test strains. The presence of a lytic zone or plaque formation showed that a particular strain is sensitive to the phage.

For the generation of the lysogen from the strains which produced spores, the method described by Hopwood et al., 1985 (Hopwood, D. A., Bibb, M. J., Chater, K. F., Kieser, T., Bruton, C. J., Kieser, H. M., Lydiate, D. J., Smith, C. P., Ward, J. M. and Schrempf, H. 1985 Genetic manipulation of Streptomyces: A laboratory manual. The John Innes Foundation, UK) was followed. However, for the isolation of lysogens from non-sporulating strains, the cells from the lysed area were collected and suspended in a sterile phage buffer and plated on a novel nutrient medium (as herein before defined). The growing colonies were tested for the presence of bacteriophage by standard methods, such as Southern hybridization using the DNA of the phage PIS136 as a probe or by spotting the putative lysogens on the lawn of a phage sensitive strain and then observing the zone of lysis around the spotted cells.

The lysogens thus obtained were tested for altered properties, or for mutation in the substrate utilization pathway or for the loss of pigment production or spore formation, by the standard method described by Hopwood et al. 1985 (Hopwood, D. A., Bibb, M. J., Chater, K. F., Kieser, T., Bruton, C. J., Kieser, H. M., Lydiate, D. J., Smith, C. P., Ward, J. M. and Schrempf, H., 1985 Genetic manipulation of Streptomyces: A Laboratory manual. The John Innes foundation, U.K.). The lysogens that were defective in the utilization of one or more substrates tested were further checked for the presence of the bacteriophage by Southern hybridization using total phage DNA as a probe.

The original lysogen Saccharomonospora PA136 produces green pigment. However, variants producing yellow pigment or no pigment were obtained from the original green pigment producing strain of Saccharomonospora PA136. The variant strains also undergo autolysis and produce the phage PIS136. However, the lysates of yellow and no pigment producing variants and the phage PIS136 purified from these lysates showed a relatively narrow host range compared with that showed by the phage preparation from the green pigment producing lysate. Furthermore, from the digestion of the phage DNA by several restriction enzymes it became apparent that a region of the phage DNA changes its orientation and this change in orientation is due the inversion of one of the DNA fragment. The inversion of this phage DNA or polynucleotide fragment appears to be the cause of the reduced host range shown by the phage preparations obtained from yellow pigment or no pigment producing variants.

Properties of the Strains Saccharomonospora PA136

Utilization of compounds: (a) Sodium chloride; (b) Hypoxanthine; (c) Hypo-xanthine+0.3% glucose; (d) Tributyrine; (e) Xylitol; (f) Thallous acetate; (g) Thallous acetate+0.1% glucose; (h) Propanol; (i) Butanol-1,3 diol; (j) D-fucose; (k) Salicin; (l) Arabinose; (m) L-asparagine; (n) Phenylalanine; (o) L-serine; (p) Sodium benzoate;

Growth at 20° C. to 55° C. on an agar plate. It grows at pH range of 5.5 to 9.0. Catalase positive. It produces the following extracellular enzymes: (a) Lipase (C14); (b) Leucine arylamidase; (c) Valine arylamidase; (d) Cystein arylamidase; (e) Trypsin; (f) Chemotrypsin; (g) Acid phosphatase; (h) Naphthol As-B1-phosphophydrolase; (i) α glucosidase; (i) β-glucosidase.

The chemical composition of the total cell comprises meso-di-aminopimelic acid, Arabinose, Galactose, Phosphatidyl glycerol, di-phosphatidyl glycerol, Phosphatidyl ethanolamine, Hydroxyphastidyl ethanolamine, Phosphatidyl inositol, Glycolipids, Sugar contain unidentified group of phospholipids.

Major amount of 16 carbon iso and antiso fatty acids of branched and straight chain carbon compounds are present. It does not utilise sucrose. Single lateral white spores are formed. It mostly produces diffusable pigment that is green, orange or yellow. Sometimes the strain Saccharomonospora PA136 does not produce any pigment at all. At times the pigment is non-diffusable. However, the pigments produced by the strain Saccharomonospora PA136 are water-soluble. The pigments are insoluble on ether, ethanol, methanol, butanol, isopropanol, benzene, ethyl acetate, chloroform and acetone. It is partially soluble in phenol.

Based on the properties such as meso-diaminopimelic acid, major amounts of 16 carbon iso and antiso fatty acids as well as arabinose and galactose as major sugar the strain producing green pigment was identified as a species of Saccharomonospora.

The novel growth medium used in the incubation and purification of the colonies was prepared by mixing the appropriate quantities of the following chemicals and complex media components selected from Beef extract or Lab Lamco, Yeast extract, Tryptose, Proteose peptone, Soluble starch, Dextrose, and traces of Cobalt chloride or Cobalt nitrate and Ferric ammonium citrate. The composition when established and dissolved in double glass-distilled water, at room temperature, has a pH from about 6.0 to 6.6. This medium when used as it is, or after adjusting the pH between 7.0 and 7.2 by using 1N Sodium hydroxide such as a universal medium for the growth of large number of actinomycetes genera, other Gram+ bacteria, some Gram- bacteria and for several groups of fungi. The growth medium of the invention is a universal growth medium, particularly useful for fastidious organisms of the genera Actinomadura, Amycolatopsis, Anthrobacter, Brevibacterium, Corynebacterium, Rhodococcus, Streptomyces, Streptoverticillium, Saccharomonospora, Microtetraspora, Micromonospora, Nocardia, Nocardiodes, slow and fast growing Mycobacteria, Bacillus, Escherichia, Pseudomonas as well as several other slow growing but yet unidentified actinomycetes and several groups of fungi. However, in the context of the present invention, the medium will be described particularly in relation to its usefulness as a growth medium for strain of Saccharomonospora.

The process for the preparation of growth medium of the present invention comprises mixing of A, B and C, i.e. macronutrients, micronutrients and trace elements in the quantities mentioned as below:

A. macronutrients in the form of assimilable carbon sources such as:

1. Lab Lamco or Beef extract 8–12 gm
  2. Starch 1–2 gm
  3. Dextrose 10 to 12 gm and
  also in the form of assimilable nitrogen sources such as:
  1. Proteose peptone 1–3 gm
  2. Tryptose 1–3 gm B. micronutrients selected from yeast extract 1–3 gm, and C. trace elements selected from:

1. Cobalt chloride or nitrate 5–10 mg
  2. Ferric ammonium citrate 5–10 mg
  3. Magnesium sulphate or chloride 1–10 mM
  4. Calcium chloride or nitrate 0–10 mM;
  and thereafter making the volume to 1000 ml by the addition of double-distilled water.

In an embodiment, the present medium may contain macronutrients such as carbon in the form of Lab Lamco or Beef extract, starch and dextrose, nitrogen in the form of proteose peptone and tryptose, micronutrients such as vitamins in the form of yeast extract, trace elements such as cobalt chloride or cobalt nitrate and ferric ammonium citrate and double glass-distilled water. Purified agar, calcium and magnesium may be added optionally when required.

One of the most important aspects in the preparation of the growth medium is the addition of extra carbon source to the medium. It is well known that glucose enters the metabolic pathway without any modification thus it is a preferred substrate of carbon for most of the organisms and gets utilized very quickly. However, high concentration of glucose in the medium can have adverse effect because glucose changes the osmolarity of the medium. Glucose/dextrose concentration in the medium is also influenced by autoclaving and long incubation period. Many of the actinomycetes genera are relatively slow growing thus there is a need to provide an additional carbon source which can release glucose/dextrose slowly and steadily for longer period. Looking at the properties of actinomycetes and some fungi, starch was chosen as an additional source of carbon because most of the organisms listed above can utilize starch, albeit slowly. Another important aspect of the present invention is the supplementation of trace elements such as cobalt and iron. Crucial role played by trace elements in the growth of an organism is a well-established fact. However, none of the media listed above have trace elements as part of their component.

The concentration of the different macro and micro nutrients used in the medium of the present invention are as follows: the macronutrient are: Lab lamco 8–10 gm or Beef Extract 10–12 gm, proteose peptone 1–3 gm, tryptose 1–3 gm, dextrose 10–12 gm, soluble starch 1–2 gm, and the micronutrients are Yeast extract 1–3 gm and trace elements are Cobalt chloride or nitrates 5–10 mg, ferric ammonium citrate 5–10 mg, magnesium sulphate or magnesium chloride 5–10 mM, calcium chloride or calcium nitrate 5–10 mM, double glass distilled water 1000 ml, pH 6.8 to 7.2. The addition of calcium and magnesium ions is optional, its presence or absence does not particularly affect the growth of every organism.

The comparison of Tryptic Soya broth medium with different supplements, basically a comparison of the growth of PA136 and lysis thereupon is depicted below in Table 1. The phage is purified from the lysed culture of Saccharomonospora strain PA 136. The novel medium allow lysis to take place within 96 hours. However, the TSB medium takes 144 hours and even then, lysis may not be complete. Incomplete lysis results in poor phage yield.

| Media | Incubation time in hour 30° C. → | | | | | | | | | | | |
|---|---|---|---|---|---|---|---|---|---|---|---|---|
| | 24 hours | | 46 hours | | 72 hours | | 96 hours | | 120 hours | | 144 hours | |
| ↓ | Growth | Lysis | Growth | Lysis | Growth | Lysis | Growth | Lysis | Growth | Lysis | Growth | Lysis |
| TSB | ++ | − | +++ | − | ++++ | − | ++++ | − | ++++ | +/− | ++++ | + |
| TSB + 0.5% Dextrose + 0.5% Beef extract + Trace elements | ++ | − | +++ | − | ++++ | − | ++++ | − | ++++ | +/− | ++++ | − |

-continued

| Media | Incubation time in hour 30° C. → | | | | | | | | | | | |
|---|---|---|---|---|---|---|---|---|---|---|---|---|
| | 24 hours | | 46 hours | | 72 hours | | 96 hours | | 120 hours | | 144 hours | |
| | Growth | Lysis | Growth | Lysis | Growth | Lysis | Growth | Lysis | Growth | Lysis | Growth | Lysis |
| TSB + 0.5% Dextrose + 0.5% Beef extract + No Trace Elements | ++ | − | +++ | − | ++++ | − | ++++ | − | ++++ | +/− | ++++ | + |
| Novel medium + Trace element | + | − | ++ | − | +++ | +/− | ++++ | ++ | | | | |
| Novel medium + No Trace element | + | − | +++ | − | +++ | +/− | ++++ | ++ | | | | |

Legend:
+ = Poor growth
++ = Normal growth
+++ = Good growth
++++ = Stationary phase
+/− = beginning of lysis
++ = complete lysis
+ = poor lysis Trace Elements:

| Ingredient | Amount (mg/l) |
|---|---|
| $ZnCl_2$ | 40 |
| $FeCl_3.6H_2O$ | 200 |
| $CuCl_2.2H_2O$ | 10 |
| $MnCl_2.4H_2O$ | 10 |
| $Na_2B_4O_7.10H_2O$ | 10 |
| $(NH_4)_6MO_7O_{24}.4H_2O$ | 10 |

The process of the present invention is illustrated in the examples given below which should not, however, be construed to limit the scope of the present invention.

EXAMPLE 1

Ten grams of soil samples were collected from a depth of 15 inches below the surface of active compost heap from Northumberland, a county in UK and from Tokyo, Japan. The samples were first air dried for 8 days at room temperature so as to kill those organisms that are sensitive to drying and then heated at 110° C. for 1 hour and cooled to the room temperature. One gram of the sample collected and pretreated as above was suspended in sterile water and vortexed. One ml of this suspension was plated on the medium containing sodium salt of Humic acid 10 g, Calcium carbonate 0.02 g, Ferrous sulphate 0.01 g, Potassium chloride 1.7 g, Magnesium sulphate 0.05 g, Disodium Hydrogen phosphate 0.5 g in distilled water at pH 7.2 and was supplemented with cycloheximide 50 μg/ml and mystatin 50 μg/ml, nalidixic acid 20 μg/ml, penicillin G 0.8 μg/ml and polymyxin B 4 μg/ml. The plates (21 plates) were incubated at a temperature between 25° C. and 55° C. (three plates each at a temperature difference of 5° C.) for a period ranging between 2–5 weeks. Each colony from the plate was subcultured on a medium containing Beef extract 12 g, Tryptose 2 g, Yeast extract 2 g, Proteose peptone 2 g, Dextrose 10 g, Calcium nitrate or Calcium chloride 10 mM, Magnesium chloride or Magnesium sulfate 10 mM, Ferric ammonium citrate 5 mg, Cobalt chloride or Cobalt nitrate 5 mg and Soluble starch 10 mg, all in 1000 ml of distilled water and the pH of the medium was maintained at 7.2. The culture plates were incubated at 30° C. and the colonies producing green pigments were purified on the above said medium. All the colonies that produced green pigment were plated on above said medium (which is a subject matter of co-pending application) in a plate or in a slant using McCartney's bottles. A set of each isolate was also preserved in glycerol mixed with the above said medium at temperatures below −20° C. The colonies producing green pigment thus obtained were identified by the standard procedures such as morphology, substrate utilization such as carbon source and nitrogen source, production of extracellular enzymes and chemical composition of the total cell (chemotaxonomy). The presence of single lateral white coloured spore, meso-diaminopimelic acid; arabinose and galactose as total sugar but no mycolic acid and major amount of 16 carbon iso and antiso fatty acids, classified the strain as a member of the group actinomycetes, and designated the strain as a species of the genus Saccharomonospora.

EXAMPLE 2

The phage PIS136 was isolated by the following procedure. The strain Saccharomonospora PA136 as obtained above was grown in the above said medium for 5 days and incubated at 30° C. and thereafter was shaken at 200 rpm. After 5 days of growth the culture was incubated at 39° C. for 4 hours. This incubation allowed the culture to lyse. The lysate thus obtained was treated with chloroform (3 percent final concentration). Chloroform kills the remaining unlysed live bacteria and also helps in the lysis of semilysed cells. To the lysate thus obtained, sodium chloride to the final concentration of 0.5 Molar was added, dissolved by slow shaking and incubated in ice for 1 hr. The mixture was then centrifuged at 8000 g for 30 minutes at 4° C. and the supernatant was collected. In the supernatant thus obtained Polyethylene glycol 8000 was added to the final concentration of 10% and dissolved to completion at very low speed to avoid any damage to the phage particles. This suspension was incubated for 17 to 18 hrs at 4° C. The precipitate thus formed was pelleted at 10,000 g for 25 minutes at 4° C., suspended in phage buffer and left for 24 hrs at 4° C. After remixing the suspension, an equal amount of chloroform was added, mixed thoroughly but slowly to precipitate polyethylene glycol and pigments and incubated at 4° C. for 8 hrs. The suspension thus obtained was centrifuged again at 14,000 rmp at 4° C. for 15 minutes and the upper aqueous phase was collected in a fresh centrifuge tube and the process was repeated. The aqueous phase thus obtained was purified in a glycerol gradient containing 40% glycerol 3 ml and 5% glycerol 4 ml (dilutions were made in the phage buffer), and 3 ml of phage suspension. Pelleting was done at 35,000 rpm for 4.5 hrs at 4° C. in a standard SW41 rotor. The Pellet thus obtained contained phage, which was resuspended in the phage buffer. The glycerol pellet as obtained above was purified using a gradient of cesium chloride solutions made in the phage buffer. The step gradient was made in a centrifuge tube from three 2 ml solutions with densities of 1.360, 1.490 and 1.600 gm cm$^{-3}$. The phage suspension, which was obtained as aqueous phase earlier, was loaded on top of the gradient solution. The gradient was centrifuged at 30,000 rpm for 4.5 hrs at 16° C. The phage was banded between the 1.600 to 1.490 and was removed by puncturing the side of the tube and diluted in the phage buffer. The phage suspension was dialysed against the phage buffer which contains 25 mM Tris.HCl, 10 mM Magnesium sulphate and 10 mM Calcium nitrate or chloride at pH pf 7.5, and temperature of 4° C. for 24 hrs and was then used for further studies. Transmission Electron Microscopy confirmed the presence of a bacteriophage that has a hexagonal head and long contractile tail in the lysate as well as in the pellet obtained either by glycerol gradient purification or by Cesium chloride gradient purification.

EXAMPLE 3

To study the host range, the bacterial tests strains which produced spores (as per Table 1) were grown on a medium containing: Yeast extract-2 g; Malt extract 10 g, Glucose 4 g, Calcium carbonate 2.0 g, Agar 1.2% and 1000 ml double distilled water at pH 7.2. The plates were incubated at 25° C.–30° C. until sporulation occurred. Spores were collected in the phage buffer by scrapping the sporulating surface, were mixed by vortexing and the suspension was filtered through sterile non-absorbent cotton wool. It was observed that 0.2 ml of slightly turbid solution produced a confluent lawn. In a separate sterile tube 0.2 ml of the spore suspension was diluted further by adding 750 $\mu$l of phage buffer and 50 $\mu$l of 1×10$^9$ pfu/ml of phage suspension (pfu-plaque forming unit). After mixing gently but thoroughly, the whole suspension was left undisturbed for 1 h at room temperature. After 1 h of incubation 2 ml of the medium described in the co-pending application, containing 0.3% agar, 10 mM of calcium nitrate and magnesium chloride was added, mixed gently and poured on predried medium. The medium temperature was less than 45° C. and the suspension spread evenly on the plate. The plate was left undisturbed for 1 hr and then incubated at 25° C.–30° C. Presence of clear or turbid spots or plaques indicated the presence of phage, which confirmed that the bacterial test strain is sensitive to the phage infection. One can also allow the sport to germinate before infecting it with phage.

EXAMPLE 4

To generate lysogens, 10 $\mu$l–20 $\mu$l of the phage suspension thus obtained in example two or the phage lysate was spotted on the lawn of the strain to be tested, for lysogen formation. After the suspension was completely dried the spotted area was marked and was allowed to sporulate (if the test strain produces spore) or incubate for 5–6 days. Spore/mycelial suspension was diluted in phage buffer to get single colonies. The single colonies were either replica plated on the lawn of sensitive/test strain or were individually spotted on pre-seeded plate. The plates were allowed to grow, and any colony that produced a zone of lysis was considered as subject to further tests as a lysogen. Some of the lysogens were also found to by auxotrophs and lacked the property of synthesizing either sugars or amino acids e.g. lactose, galactose, glucose arginine, methionine, tryosine, leucine etc. The auxotrophy observed was due to a mutation in the metabolic pathways of the sugar/amino acids caused by the phage PIS136. Mutation in more than one pathway confirm that the phage PIS136 integrates in the host genome at random sites. This property of mutation and random transposition was clearly demonstrated in *Streptomyces coelicolor, Streptomyces albus* and *Mycobacterium fortuitum*.

EXAMPLE 5

The DNA of phage PIS136 was purified using a standard method for phage DNA purification but the method was modified to suite the phage PIS136. Herein the phage suspension containing about 1×10$^9$ phage particles per ml was mixed with a EDTA (Ethylene-diamino-tetra-aceticacid) solution to five a final concentration of 50 mM. This suspension was mixed with final concentration of proteinaseK 100 $\mu$g/ml, $\beta$-mercaptoethanol 14 mM and 0.5% of SDS and incubated at 37° C. for 2 hrs. After that Triton X100 to the final concentration of 1% was added and the solution was incubated for 30 minutes at 53° C. In this mixture SSC (sodium chloride 3 M and TriSodiumCitrate 0.3M) to the final concentration of 1X was added and the mixture was incubated at 65° C. for 30 minutes. After slow cooling to room temperature sodium chloride to final concentration of 0.25M was added and after mixing thoroughly an equal volume of TE saturated phenol (Tris HCl pH 8.0, 10 mM and EDTA pH 8.0, 1 mM) was added. After thorough mixing of the solution, it was centrifuged at high speed and the upper aqueous layer was collected. The interface was extracted once again with TE and the process of phenol treatment was repeated. The aqueous layer was further purified with two sets of chloroform treatment and then the phage DNA was precipitated by twice the volume of cold absolute ethanol. After two washes in 70% ethanol at room temperature, the pellet was dried and dissolved in TE buffer. The phage DNA thus obtained was used for further studies in which, the DNA was digested by a total of 45 different restriction enzymes including restriction enzymes that are methylene sensitive. The different DNA band patterns produced by the restriction enzymes MspI, HpaII, Sau3A1, MboI, indicate that the PIS136 DNA is methylated.

EXAMPLE 6

To confirm that the phage PIS136 is integrated to the chromosomes of the putative lysogens generated in example 4 and total DNA from the strain of Saccharomonospora and other lysogens were prepared by the standard method of Hopwood et al. (Hopwood, D. A., Bibb, M. J., Chater, K. F., Kieser, T., Bruton, C. J., Kieser, H. M., Lydiate, D. J., Smith, C. P., Ward, J. M. and H. Schremf, 1985 Genetic manipulation of Streptomyces: A Laboratory Manual Publ. The John Innes Foundation Norwich, U.K.). In each case the DNA was digested by those restriction enzymes which cut within the phage genome, the DNA bands were separated on a agarose gel, transferred to a nylon membrane using a standard methods and Southern hybridization was performed using a standard published method. Total DNA of the phage PIS136 or any one of the fragments of PIS136 was used as a probe. Presence of the PIS136 DNA hybridizing band shows that the phage PIS136 has integrated into the genomes of the putative lysogens of other host strains as well as in the Saccharomonospora PA136.

EXAMPLE 7

The inversion characteristic of the phage PIS136 DNA was checked by isolating the phage DNA separately from the lysates of the yellow and green variants of the Saccharomonospora PA136. These two DNA preparations were subjected to the restriction digestion by ClaI, NcoI and PvuII, and the resulting DNA fragments were separated on an agarose gel, and transferred onto a nylon membrane using a standard protocol. Southern hybridization was performed using the total phage DNA as a probe. A ClaI fragment of the white coloured phage of about 3.8 kb was represented by two fragments of about 2 kb and 1.8 kb in the phages produced by the white coloured variant. This result indicates that after inverting to other orientation the 3.8 kb ClaI fragment has acquired an extra site for the enzyme ClaI. As the ClaI fragments of the two types of the phage preparation are 100% homologous, the phages produced by the variants of the strain Saccharomonospora PA136 which produce yellow pigment and green pigment are the same.

EXAMPLE 8

Mutants in the antibiotic pathways such as rifamycin and actinorhodin were generated using the bacteriophage/phage. The 10 $\mu$l of phage preparation (4.5×10$^8$ plaque forming units per ml) was spotted on the lawn of *Streptomyces coelicolor* (for actinohodin) and *Amycolatopsis mediterranei* (for rifamycin) and incubated at 30° C. for five days. Isolated colonies growing on the spotted area were purified in a fresh medium plate and allowed to row for 3–5 days. Either spore or mycelium suspension was prepared from the isolated colonies in the phage buffer and plated on fresh plates containing nutrient medium of the present invention to obtain single colonies. Randomly selected colonies were checked for lysogeny, for mutation in the metabolic pathways by Southern hybridization and for the production of metabolic products. Several lysogens that showed mutation in antibiotic pathways were obtained. Several other mutants that were defective in amino acid biosynthesis were also obtained.

EXAMPLE 9

To confirm that the genetic material of the phage PIS is covered with a protein, glycerol purified phage preparation was mixed with protein loading buffer with the final concentration of different components as follows: Tris buffer pH 6.8–15.6 mM, glycerol 2.5% sodium dodesyl sulphate 0.5% Bromophenol blue 0.0125%. The samples were heated for 15 minutes in a boiling water bath, chilled immediately in ice water for 10 minutes and centrifuged at 13000 rpm for 5 minutes. Samples were loaded on a 14% polyacrylamide gel and the proteins separated in a running buffer containing: Tris base 3 gm/liter, glycine 14.4 gm/liter, sodium dodesyl sulphate 0.1% pH of the gel running buffer was 8.3. Gel was stained in an aqueous solution containing, in 100 ml: methanol 50 ml, acetic acid 10 ml, Coomassie Brilliant Blue R250 0.25 gms, water 40 ml, for 2 hours, at 42° C. The gel was de-stained with several changes of solution containing in 100 ml: methanol 10 ml, acetic acid 5 ml, water 85 ml. The total phage coat protein is represented by 9 bands of approximate molecular weight in kilodalton of 60, 57, 42, 36, 30, 29, 22, 20 and 14, where 60 and 57 kilodaltons protein are major phage coat protein and are present in very high concentration.

EXAMPLE 10

Molecular size of the genetic material of the phage, which is a double stranded DNA, was calculated using four restriction enzymes: NotI, NheI, SNaBI and ScaI. The DNA fragments obtained by digesting the genetic material of the phage PIS 136 with the four restriction enzymes in different permutations and combinations, was separated either on a normal agarose gel or on a Pulse Field Gel Electrophoresis setting running conditions of 1.5 volts/cm$^2$ of the gel for 15 hours at 14° C. and then 2 volts/cm2 for 3 hours at an angle of 120° and switching time of 5 seconds to 60 seconds with linear ramping. Gel was stained in ethidium bromide and molecular weight was calculated using standard molecular weight markers. The molecular size of PIS 136 DNA is about 90 kilobases. The guanidine and cytosine ratio of the PIS 136 genome was measured using standard methods available and documented in the art and was found to be 69 to 71 mol %. The bacteriophage PIS 136 is resistant to several restriction enzymes for which one would think that the high guanidine and cytosine ratio would provide a sensitive site.

EXAMPLE 11

The phage PIS 136 was isolated and purified from the lysogens of *Amycolatopsis mediterranei* after inducing with ultraviolet light in order to confirm that some other *actinomycetes* strain an also be used as a host to study phage biology. Phage purification has been described in example 2. Lysogenes of *Amycolatopsis mediterranei* were generated as described in Example 4. The results provide that the *Amycolatopsis mediterranei* can be used as an alternate host for the propagation and genetic studies of the phage. These studies include the growth of the bacteriophage within the host, receptor for the phage that helps the phage enter the host, factors that may help the phage to establish itself inside the host, etc. Modification of these factors can help to increase the host range of the phage, which will increase its utility as a vector system or genetic tool. As the strain *Amycolatopsis mediterranei* produces the important antibiotic rifamycin and its analogues, with the help of available art one can study the metabolic pathway of the antibiotics and also the effect of blocking the function of a particular gene of the pathway in the production of an antibiotic. One can further use the phage PIS 136 to block many other antibiotic pathways which normally run in parallel to the one described in the literature and a person with ordinary skill in the art can perform these experiments. The art can be transferred to any other organisms to which the phage PIS 136 or its derivatives generated by using a standard and well-documented procedure may use as a host. All the above methods will have an effect on the antibiotic production and in many cases several new metabolites will be obtained.

EXAMPLE 12

In this example, the antibiotic production properties of *Amycolatopsis mediterranei* lysogens were studied and compared with one produced by the non-lysogen. The example demonstrates that the phage PIS 136 indeed modulates the antibiotic production. Several lysogens of the strain *Amycolatopsis mediterranei* were generated by the method described in Example 4. The lysogens were grown on a known manner having the following composition (amounts in gm/liter). Soybean meal (defatted) 5.0; calcium carbonate 9.0, pH 7.2; (after autocleaving) filter sterilised sodium barbiturate 1.5, dextrose 50.0; potassium dihydrogen phosphate 3.0; ammonium sulphate 7.0; magnesium sulphate 1.0; copper sulphate 3.3 mg; ferrous sulphate 10.0 mg; manganese sulphate 4.0 mg; zinc sulphate 50.0 mg. The 500 ml flasks containing 50 ml medium was inoculated with a two day old culture and incubated at 30° C. at 200 rpm (rounds per minute). Five flasks for each hydrogen were inoculated. The flasks were removed after a two-day interval or as colour of the medium changes from almost colourless to different shades of yellow or red. The cells and other medium components are removed by centrifugation at 4° C. and pH of the supernatant was adjusted to 2.2 or about 2.0 with the help of 6 molar sulphuric acid. The broth was extracted with 0.2 volumes of ethyl acetate and the extraction was repeated four times. All the ethyl acetate extracts were mixed together and concentrated to the final volume of 1.5 ml at 30° C. The fermentation products were separated on fluorescent silica coated thin layer chromatography plates, Emerck number 1.05554 using solvent systems: chloroform 6: methanol 6: water 1 and chloroform 6: methanol 6: water 1: ammonia 1. The plates were then visualised under short and long wavelength ultraviolet lights. Some of the metabolites produced by the lysogens are different from those produced by the non-lysogenic control. These metabolites either showed different fluorescent properties or if the fluorescence was the same as in the control, the differences in their relative mobility was very clear when studied by thin layer chromatography as shown in FIG. 1.

EXAMPLE 13

Fermentation of some of the lysogens was repeated in order to show that the phage PIS 136 could affect the antibiotic production by changing its integration site within the host. Procedure to extract the fermentation products and analyse them has been described in Example 12. Two of the lysogens produced metabolites that were different from the previous batch. Analysis of the DNA of the lysogens clearly show that the phage PIS 136 has changed its position during the period spent in fermentation and the change in the position of the phage within the host genome seems to have profound effect on the antibiotic biosynthetic pathway. The effect in the biosynthesis is clearly visible because the metabolites produced are different from the previous batch. Explanation for this change in the position of the phage is due to the transposogenic nature of the phage genome. Perhaps during replication, the phage is capable of changing its position and moving to a new site, thereby affecting different sets of genes. This property of the phage can be used by anyone who is aware of established art in molecular biology to generate mutations which may be of use to improve antibiotic biosynthesis, in the production of hybrid antibiotics, and new metabolites. Mutations which will be useful for the study of general biology and physiology of any organism to which the phage PIS 136 or its derivatives, constructed by using available art such as polymerase chain reaction or cloning the whole phage into a new or into the vectors already available or a fragment of the phage genome into a vector or even the naked DNA by itself, may use as a host.

EXAMPLE 14

Lysogens of *Streptomyces coelicolor* were checked for different mutated phenotypes. The strain *Streptomyces coelicolor* produces blue pigmented antibiotic actinorhodin and another red pigmented antibiotic. Thus, the colour production is a direct indication of the antibiotic production. Further, the strain produces spores that are gray in colour. Therefore, any mutation either in the antibiotic pathway or in the sporulation pathway will be seen as a change in the colour of the pigment of non-sporulating mycelium or white spores. Further, the strain *Streptomyces coelicolor* can grow in a medium containing 34% sucrose. The lysogens of the *Streptomyces coelicolor* were obtained as described in Example 4. After confirming that the phage PIS 136 has integrated in the chromosome of the host by any method well documented in the art or as described in example 2, mutant properties of the lysogens were checked by using well documented art in the field. A set of mutants did not produce any pigment and also the spores were white in colour. Another set of mutants which grew much faster than the control non-lysogen and also lacked pigment. Another set of mutants did not produce any pigment but sporulated profusely with grey spores. Yet another set of mutants did not produce any pigment or spores. However, one set of mutants did not produce any pigment but spores which were sparse and white. Yet another set of lysogens did not grow in the medium containing 34% sucrose indicating mutation in the cell wall or in the sucrose metabolic pathway. The sporulation property did not change even in the specific sporulation medium described in the art. The onset of sporulation is extremely important for antibiotic production. Therefore, by using phage PIS 136, one can obtain mutants in any host that the phage PIS 136 infects. This enables the study of the regulation of the antibiotic biosynthetic pathway or any other pathway which otherwise may be difficult to study.

EXAMPLE 15

The impact of the phage PIS 136 on the study of pathogenic organisms may be several fold. In this example, lysogens of *Mycobacterium fortuitium,* which is an opportunistic human pathogen, were generated by the method described in Example 4. The lysogeny was confirmed by conventional processes and by the method described in Example 6. The mutant properties were checked according to methods well documented in the art. Some of the lysogens had lost the property to segment and had become mycelial. As the septation involves several biochemical changes in the cell, the mycelial mycobacteria are likely to be non-pathogenic. Further, these mutants will also be useful in unravelling the biochemical pathways that may play major role in septation and also find out the signal that orders the cell to undergo septation. Therefore, one can study the mechanism of pathogenicity of those pathogenic organisms that the phage PIS 136 infects. It is also possible to find mutants that have lost the pathogenicity but will survive long enough to generate immune response. Such strains can be used as vaccines and such use is well documented in the art. The phage PIS 136 can integrate within the cell that it infects and can therefore be used as a tool to identify the mutant and also identify the gene in which mutation has occurred. The use of transposon as a signature tag to identify mutants is well documented in the art. However, a bacteriophage has never been used as a signature tag system to allow the study of pathogen growth within the host.
Preparation of the Novel Medium

EXAMPLE 16

Following media components and analytical grade chemicals were mixed at room temperature. Beef extract 10 gm, yeast extract 2 gm, protease peptone 2 gm, tryptose 2 gm, dextrose 10 gm, Soluble starch 1 gm, Cobalt chloride 5 mg, ferric ammonium citrate 5 mg, double glass-distilled water 1000 ml, Agar 11 gm, pH 7.0. The medium was sterilized at 20 Lb per inch square (steam) pressure for 20 minutes. This medium supported the growth of Actinomadura sps, Amycolatopsis sps, Arthrobacter sps, Brevibacterium sps, Corynebacterium sps, Rhodococcus sps, large number of Streptomyces sps, Saccharomonospora sps, Saccharopolyspora sps, Microbispora sps, Microtetraspora sps, Micromonospora sps, Nocardia sps, Nocardiodees sps, and Streptosporangium sps, Streptococcus sps, Staphylococcus sps, Bacillus sps, Eschericia sps, Pseudomonas sps and several groups of fungi. Species of mycobacteria did not grow very well in this medium. Poor sporulation of some species of Streptomyces, Microbispora, Microtetraspora was observed after 15 days of growth, however most of the strains listed above did not sporulate at all and produced good mycelial growth after 3 days of incubation, thus establishing that the medium will be very useful for all the actinomycetes and other groups of bacteria and fungi. The species of Saccharomonospora grew well in this medium upto 55° C.

EXAMPLE 17

The medium composition was Beef extract 12 gm, yeast extract 2 gm, proteose peptone 2 gm, tryptose 2 gm, dextrose 10 gm, Cobalt chloride 5 mg, ferric ammonium citrate 5 mg, double glass distilled water 1000 ml, Agar 11 gm, pH 7.0. The medium was sterilized at 20 Lb per inch square (steam) pressure for 20 minutes. Slow growing species of Actinomadura, Streptosporangium, Microbispora and Microtetraspora grew poorly as compared to the medium composition which was supplemented with 10 gm/1000 ml beef extract and starch as described above.

EXAMPLE 18

The medium composition was Beef extract 10 gm, yeast extract 2 gm, proteose peptone 2 gm, tryptose 2 gm, dextrose 10 gm, Soluble starch 1 gm, Cobalt chloride 5 mg, ferric ammonium citrate 5 mg, double glass distilled water 1000 ml, Agar 11 gm, pH 7.0. The medium was sterilized at 20 Lb per inch square (steam) pressure for 20 minutes. Keeping rest of the media component the same, as described above, dextrose was replaced with 1% v/v glycerol as final concentration and 1.0 gm citric acid was added. These replacement and addition facilitated the growth of wide range of fast growing mycobacteria and at least one slow growing mycobacterium that is M.bovis BCG (Bacillus Calmette Guerin).

Advantages of the Present Invention

The bacteriophage obtained from the examples given above have following advantages:
1. The bacteriophage or its DNA may infect several microorganisms unlike almost all the bacteriophages described by others.
2. The bacteriophage or its DNA described in this invention may specifically by used for infecting the genera of actinomycetes.
3. The bacteriophage may be used for generating random mutations in the wide range of microorganism, even in those microorganisms where classical methods do not work.
4. The bacteriophage described in this invention may be used for generating mutations in the specific metabolic pathways in order to obtain new compounds.
5. The bacteriophage may also be used for mobilising genes from one organism to other and also to specific location in large number of organisms including plants.
6. The bacteriophage may also be used to block a metabolic pathway temporarily. This step allows the intermediate product of the pathway to accumulate in the system, which then is used, by some other functional metabolic pathway. This process results in to the accumulation of new metabolic products.
7. The phage or its DNA may also be used to generate mutations in pathogenic organisms like mycobacteria to produce vaccine strains.
8. The medium supports the growth of several groups of fungi including the fastidious group basidiomycetes. The medium shortens the growth time required and as the medium does not support sporulation, it is useful whenever large mycelial culture is required.
9. The medium composition described in this invention is a synergistic composition, due to which, the medium helps in the faster growth of wide range of organisms, does not allow sporulation and can withstand relatively high growth temperature without affecting the growth pattern and after some modifications as explained in the examples 18 and 19, even the fastidious organisms such as mycobacteria can easily be grown.

We claim:
1. A process for the isolation of a bacteriophage which comprises incubating a novel strain of Saccharomonospora deposited at DSMZ-DEUTSCHE SAMMELUNG VON MIKROORGANISMEN UND ZELLKULRTUREN GmbH bearing the accession number DSM 12317 (Indian Accession No. MTCC A0001) in a nutrient medium until the autolysis stage is reached, isolating and purifying from the medium a bacteriophage generated in the lysed culture.
2. A process as claimed in claim 1 wherein nutrient medium used for the incubation of said novel strain is selected from the Tryptic Soya agar, yeast extract and malt extract medium and a medium which comprises Beef extract or Lab Lamco, Yeast extract, Typtose, Proteose peptone, Soluble starch, Dextrose, and traces of Cobalt chloride or Cobalt nitrate and Ferric ammonium citrate and when established and dissolved in double glass-distilled water, at room temperature, has a pH from about 6.0 to 6.6
3. A process as claimed in claim 1 wherein incubation is effected for 3–6 days.
4. A process as claimed in claim 1 further comprising breaking up the proteinaceous envelope of the said isolated bacteriophage followed by recovering the polynucleotide by precipitation.
5. A process as claimed in claim 4 wherein precipitation of polynucleotide is carried out in the presence of 0.25M sodium chloride and a solution of 0.15M sodium chloride and 0.015M tri-sodium citrate, at 4° C. in presence of ethanol.
6. A process as claimed in claim 4 wherein said breaking up of proteinaceous envelope is effected by treating the said bacteriophage by proteolytic enzyme, ionic or nonionic detergent, and B-mercaptoethanol.
7. A process as claimed in claim 6 wherein the proteolytic enzyme is proteinase K or pronase.
8. A process as claimed in claim 6 wherein the ionic or nonionic detergent is selected from the group consisting of sodium dodecyl sulfate, α-[4-(1,1,3,3,-tetramethylbutyl) phenyl]-ω-hydroxypoly(oxy-1,2-ethanediyl), and octylphenoxy polyethoxy ethanol.
9. An isolated bacteriophage having a double-stranded DNA genome of about 90 kilobase pairs with a (G+C) content of 69–71 mol percent, which infects the same range of species of bacteria as phase PIS 136.
10. An isolated bacteriophage isolatable from Saccharaomonospora, having a double-stranded DNA genome of about 90 kilobase pairs with a (G+C) content of 69–71 mol percent, which lysogenizes and integrates into the genome of actinomycetes.
11. An isolated bacteriophage isolatable from Sacharaomonospora, having a double-stranded DNA genome of about 90 kilobase pairs with a (G+C) content of 69–71 mol percent, which acts as a transposon in actinomycetes.

12. A cell selected from the group consisting of cells of *Escherichia coli, Streptomyces amycolata,* Mycobacteria and Bacillus comprising the bacteriophage as claimed in claim 9.

13. A bacteriophage as claimed in claim 10 which infects actinomycetes genera.

14. A bacteriophage as claimed in claim 10 which infects *Bacillus subtilis.*

15. A cell selected from the group consisting of cells of *Escherichia cell, Streptomyces amycolata,* Mycobacteria and Bacillus comprising the bacteriophage as claimed in claim 10.

16. A bacteriophage as claimed in claim 11 which infects actinomycetes genera.

17. A bacteriophage as claimed in claim 11 which infects *Bacillus subtilis.*

18. A cell selected from the group consisting of cells *Escherichia coli, Streptomyces amycolata,* Mycobacteria and Bacillus comprising the bacteriophage as claimed in claim 11.

19. An isolated bacterial cell comprising the DNA of the bacteriophage of claim 9.

20. An isolated bacterial cell comprising the DNA of the bacteriophage of claim 10.

21. An isolated bacterial cell comprising the DNA of the bacteriophage of claim 11.

22. A cloning vector comprising the double-stranded DNA genome of the isolated bacteriophage of claim 9.

23. A cloning vector comprising the double-stranded DNA genome of the isolated bacteriophage of claim 10.

24. A cloning vector comprising the double-stranded DNA genome of the isolated bacteriophage of claim 11.

25. A cloning vector as claimed in claim 22 wherein the cloning vector comprises a plasmid.

26. A cloning vector as claimed in claim 23 wherein the cloning vector comprises a plasmid.

27. A cloning vector as claimed in claim 24 wherein the cloning vector comprises a plasmid.

28. A cell comprising the double-stranded DNA genome of the isolated bacteriophage of claim 9 wherein the cell is selected from *Escherichia coli, Streptomyces amycolata,* Mycobacteria or Baccillus.

29. A cell comprising the double-stranded DNA genome of the isolated bacteriophage of claim 10 wherein the cell is selected from *Escherichia coli, Streptomyces amycolata,* Mycobacteria or Bacillus.

30. A cell comprising the double-stranded DNA genome of the isolated bacteriophage of claim 11 wherein the cell is selected from *Escherichia coli, Streptomyces amycolata,* Mycobacteria or Baccillus.

31. A method of mutating a metabolic pathway of a bacteria comprising the step of infecting the bacteria with the bacteriophage of claim 9.

32. A method of mutating a metabolic pathway of a bacteria comprising the step of infecting the bacteria with the bacteriophage of claim 10.

33. A method of mutating a metabolic pathway of a bacteria comprising the step of infecting the bacteria with the bacteriophage of claim 11.

* * * * *